United States Patent
Mc Gowan et al.

(10) Patent No.: US 9,790,191 B2
(45) Date of Patent: Oct. 17, 2017

(54) SUBSTITUTED ACYLAMINOPYRIMIDINES AS INDUCERS OF ALPHA INTERFERON PRODUCTION

(71) Applicant: JANSSEN SCIENCES IRELAND UC, Little Island, Co Cork (IE)

(72) Inventors: David Craig Mc Gowan, Brussels (BE); Serge Marie Aloysius Pieters, Hulst (NL); Werner Embrechts, Beerse (BE); Stefaan Julien Last, Lint (BE); Tim Hugo Maria Jonckers, Heist-op-den-Berg (BE); Pierre Jean-Marie Bernard Raboisson, Rosieres (BE)

(73) Assignee: JANSSEN SCIENCES IRELAND UC, Little Island, Co Cork (IE)

( * ) Notice: Subject to any disclaimer, the term of this patent is extended or adjusted under 35 U.S.C. 154(b) by 86 days.

(21) Appl. No.: 14/431,973

(22) PCT Filed: Oct. 3, 2013

(86) PCT No.: PCT/EP2013/070619
§ 371 (c)(1),
(2) Date: Mar. 27, 2015

(87) PCT Pub. No.: WO2014/053595
PCT Pub. Date: Apr. 10, 2014

(65) Prior Publication Data
US 2015/0274676 A1 Oct. 1, 2015

(30) Foreign Application Priority Data
Oct. 5, 2012 (EP) ..................... 12187519

(51) Int. Cl.
*C07D 239/47* (2006.01)
*C07D 401/12* (2006.01)
*C07D 213/75* (2006.01)
*C07D 239/48* (2006.01)

(52) U.S. Cl.
CPC ......... *C07D 239/47* (2013.01); *C07D 213/75* (2013.01); *C07D 239/48* (2013.01)

(58) Field of Classification Search
CPC .......................... C07D 239/47; C07D 401/12
USPC ....................... 544/330; 546/268.1
See application file for complete search history.

(56) References Cited

U.S. PATENT DOCUMENTS 5,434,157 A 7/1995 Wierenga et al.

FOREIGN PATENT DOCUMENTS

| EP | 1110951 A1 | 6/2001 |
|---|---|---|
| WO | WO 2006/053109 A1 | 5/2006 |
| WO | WO 2009/067081 A1 | 5/2009 |
| WO | WO 2010/133885 A1 | 11/2010 |
| WO | WO 2012/136834 A1 | 10/2012 |
| WO | WO 2014/053595 A1 | 4/2014 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Chawla, et al. Current Research & Information on Pharmaceutical Sciences (CRIPS), 5(1), 2004, 9-12.*
Hackam, et al. JAMA, 296(14), 2006, 1731-1732.*
Bello, A., et al., "De Novo Design of Nonpeptidic Compounds Targeting the Interactions between Interferon-α and its Cognate Cell Surface Receptor", Journal of Medicinal Chemistry, vol. 51, pp. 2734-2743 (2008).
DeClerca, E., et al., "(S)-9-(2,3-Dihydroxypropyl)adenine: An Aliphatic Nucleoside Analog with Broad-Spectrum Antiviral Activity", Science, vol. 200, pp. 563-565 (May 1978).
Fried, M., et al., "Peginterferon Alfa-2$_a$ Plus Ribavirin for Chronic Hepatitis C Virus Infection", New England Journal of Medicine, vol. 347, No. 13, pp. 975-982 (Sep. 2002).
International Search Report mailed Nov. 91, 2013 for corresponding Application No. PCT/EP2013/070619.
European Search Report completed Feb. 8, 2013 for corresponding Application No. EP12187519.

* cited by examiner

*Primary Examiner* — Douglas M Willis

(57) ABSTRACT

This invention relates to acylaminopyrimidine derivatives, processes for their preparation, pharmaceutical compositions, and their use in therapy.

1 Claim, 2 Drawing Sheets

Mouse IFNa Levels in Liver

Mouse IFNa Levels in Plasma

SUBSTITUTED ACYLAMINOPYRIMIDINES AS INDUCERS OF ALPHA INTERFERON PRODUCTION

This application is a 35 U.S.C. 371 nationalization of PCT application PCT/EP2013/070619, filed Oct. 3, 2013, which claims priority to European patent application 12187519.9 filed Oct. 5, 2012, both of which are incorporated herein by reference.

This invention relates to acylaminopyrimidine derivatives, processes for their preparation, pharmaceutical compositions, and their use in therapy.

BACKGROUND OF THE INVENTION

The present invention relates to the use of acylaminopyrimidine derivatives in the treatment of viral infections, immune disorders, and cancer, or as a vaccine adjuvant, whereby the induction of interferon is desired. In the treatment of certain viral infections, regular injections of interferon (IFN-type 1) can be administered, as is the case for hepatitis C virus (HCV), For more information see reference Fried et. al. Peginterferon-alfa plus ribavirin for chronic hepatitis C virus infection, *N Engl J Med* 2002; 347: 975-82. Orally available small molecule IFN inducers offer the potential advantages of reduced immunogenicity and convenience of administration. Thus, novel IFN inducers are a potentially effective new class of drugs for treating virus infections. For an example in the literature of a small molecule IFN inducer having antiviral effect see De Clercq, E.; Descamps, J.; De Somer, P. *Science* 1978, 200, 563-565.

However there exists a strong need for novel interferon inducers having an improved safety profile compared to the compounds currently known.

BRIEF SUMMARY OF THE INVENTION

In accordance with the present invention a compound of formula (I) is provided

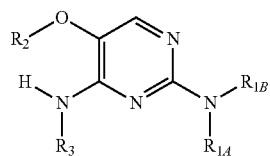

(I)

or a pharmaceutically acceptable salt, solvate or polymorph thereof, wherein
$R_{1A}$ is selected from the group hydrogen, a substituted or unsubstituted acyl, or acyloxy group,
$R_{1B}$ is selected from the group hydrogen, a substituted or unsubstituted acyl, or acyloxy group,
with the proviso that $R_{1A}$ and $R_{1B}$ are not both hydrogen,
$R_2$ is $C_{1-6}$alkyl, $C_{1-6}$ alkoxy, arylalkyl or heteroarylalkyl, each of which is optionally substituted by one or more substituents independently selected from halogen, hydroxyl, amino, di-($C_{1-6}$)alkylamino, $C_{1-6}$ alkylamino, $C_{1-6}$ alkyl, $C_{1-6}$ alkoxy, $C_{3-6}$ cycloalkyl, carboxylic acid, carboxylic ester, carboxylic amide, heterocycle, bicyclic heterocycle, aryl, alkenyl, alkynyl, arylalkyl, heteroaryl, heteroarylalkyl, or nitrile and
$R_3$ is a $C_{1-8}$ alkyl, or arylalkyl each of which is optionally substituted by one or more substituents independently selected from halogen, hydroxyl, amino, $C_{1-6}$ alkyl, di-($C_{1-6}$)alkylamino, $C_{1-6}$ alkylamino, $C_{1-6}$ alkoxy, $C_{3-6}$ cycloalkyl, carboxylic acid, aromatic or aliphatic carboxylic ester, carboxylic amide, heterocycle, aryl, alkenyl, alkynyl, arylalkyl, heteroaryl, heteroarylalkyl, or nitrile.

Figure 1A:
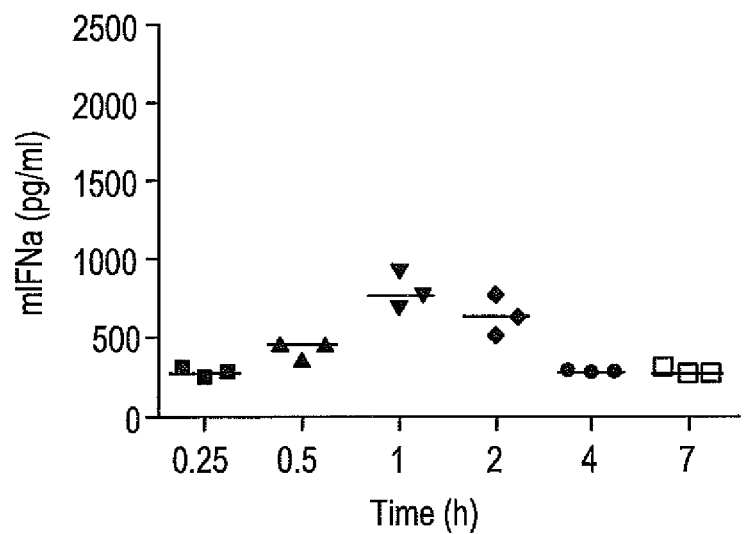
FIGS. 1A and 1B. Interferon levels measured in the liver (FIG. 1A) and in the plasma (FIG. 1B) after single oral administration of compound 1 at 15.5 mg/kg in mice.
Figure 1B:
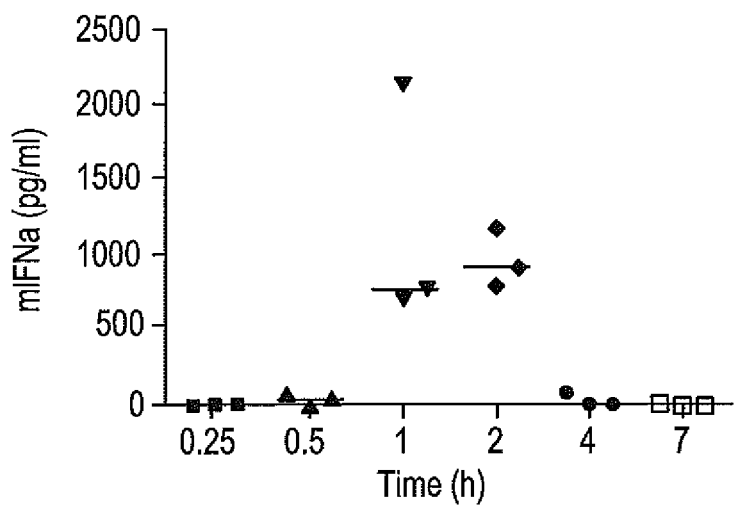
Figure 2A:
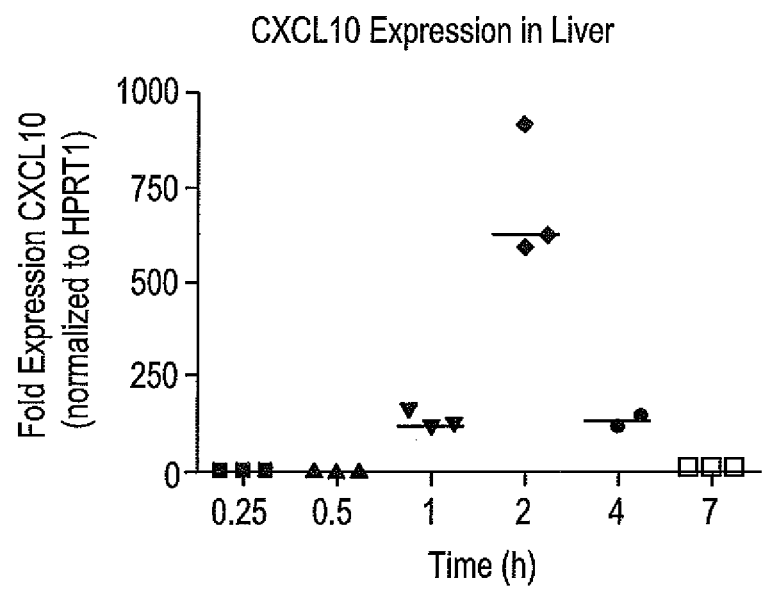
FIGS. 2A and 2B. CXCL10 expression measured in the liver (FIG. 2A)* and in the blood (FIG. 2B) after single oral administration of compound 1 at 15.5 mg/kg in mice.
Figure 2B:
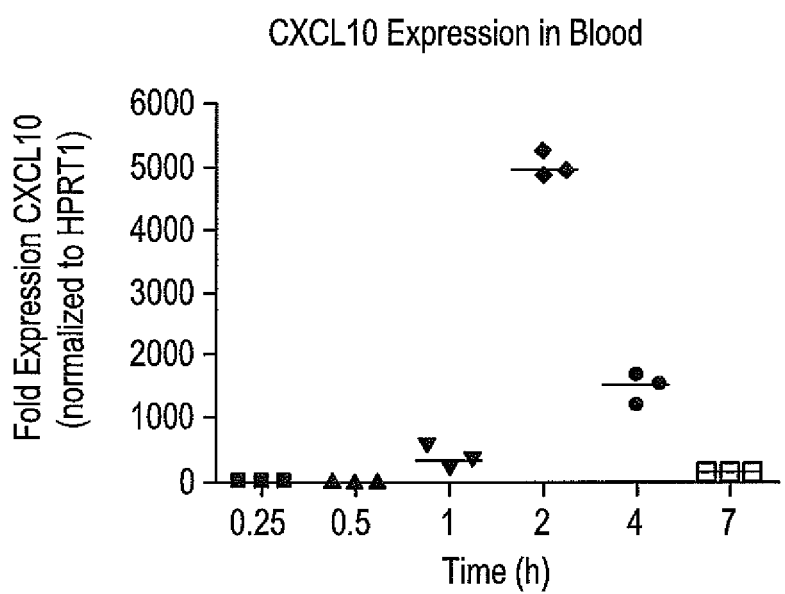

*one 4 h time point sample was removed due to high HPRT1 value

Induction of endogenous interferon and upregulation of CXCL10 was observed in the liver and blood/plasma in mice after oral administration of a single dose of compound 1.

DETAILED DESCRIPTION OF THE INVENTION

In a first embodiment the present invention provides compounds of formula (I) wherein $R_{1A}$ and/or $R_{1B}$ are substituted or unsubstituted acyl and wherein $R_2$ is $C_{1-6}$ alkyl preferably —$CH_3$ and $R_3$ is $C_{1-8}$ alkyl substituted with an alkylester.

In a second embodiment the present invention provides compounds of formula (I) wherein $R_{1A}$ and/or $R_{1B}$ are isobutyryl and wherein $R_2$ is —$CH_3$, and $R_3$ is heptan-3-yl isobutyrate.

The compounds of formula (I) in any stereochemical form and their pharmaceutically acceptable salt, solvate or polymorph thereof have activity as pharmaceuticals, in particular as inducers of interferon.

So, in a further aspect the present invention provides a pharmaceutical composition comprising a compound of formula (I) or a pharmaceutically acceptable salt, solvate or polymorph thereof together with one or more pharmaceutically acceptable excipients, diluents or carriers.

Furthermore a compound of formula (I) or a pharmaceutically acceptable salt, solvate or polymorph thereof according to the current invention, or a pharmaceutical composition comprising said compound of formula (I) or a pharmaceutically acceptable salt, solvate or polymorph thereof can be used as a medicament.

Another aspect of the invention is that a compound of formula (I) or a pharmaceutically acceptable salt, solvate or polymorph thereof, or said pharmaceutical composition comprising said compound of formula (I) or a pharmaceutically acceptable salt, solvate or polymorph thereof can be used accordingly in the treatment of a disorder in which the induction of interferon is involved.

The term "alkyl" refers to a straight-chain or branched-chain saturated aliphatic hydrocarbon containing the specified number of carbon atoms.

The term "halogen" refers to fluorine, chlorine, bromine or iodine.

The term "acyl" refers to the group defined as —(C=O)R, where R is a substituted or unsubstituted alkyl, cycloalkyl, aryl, heteroaryl.

The term "acyloxy" refers to the group defined as —(C=O)OR, where R is a substituted or unsubstituted alkyl, cycloalkyl, aryl, heteroaryl.

The term "alkenyl" refers to an alkyl as defined above consisting of at least two carbon atoms and at least one carbon-carbon double bond.

The term "alkynyl" refers to an alkyl as defined above consisting of at least two carbon atoms and at least one carbon-carbon triple bond.

The term "cycloalkyl" refers to a carbocyclic ring containing the specified number of carbon atoms.

The term "alkoxy" refers to an alkyl (carbon and hydrogen chain) group singular bonded to oxygen (e.g. methoxy group or ethoxy group).

The term "aryl" means an aromatic ring structure optionally comprising one or two heteroatoms selected from N, O and S, in particular from N and O. Said aromatic ring structure may have 5, 6 or 7 ring atoms. In particular, said aromatic ring structure may have 5 or 6 ring atoms.

The term "bicyclic heterocycle" means an aromatic ring structure, as defined for the term "aryl" comprised of two fused aromatic rings. Each ring is optionally comprised of heteroatoms selected from N, O and S, in particular from N and O.

The term "arylalkyl" means an aromatic ring structure as defined for the term "aryl" optionally substituted with an alkyl group.

The term "heteroarylalkyl" means an aromatic ring structure as defined for the term "heteroaryl" optionally substituted by an alkyl group.

"Heterocycle" refers to molecules that are saturated or partially saturated and include ethyloxide, tetrahydrofuran, dioxane or other cyclic ethers. Heterocycles containing nitrogen include, for example azetidine, morpholine, piperidine, piperazine, pyrrolidine, and the like. Other heterocycles include, for example, thiomorpholine, dioxolinyl, and cyclic sulfones.

"Heteroaryl" groups are heterocyclic groups which are aromatic in nature. These are monocyclic, bicyclic, or polycyclic containing one or more heteroatoms selected from N, O or S. Heteroaryl groups can be, for example, imidazolyl, isoxazolyl, furyl, oxazolyl, pyrrolyl, pyridonyl, pyridyl, pyridazinyl, pyrazinyl . . . .

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form. The compounds of the present invention or any subgroup thereof may be formulated into various pharmaceutical forms for administration purposes.

As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

EXPERIMENTAL SECTION

Preparation of Compound 1

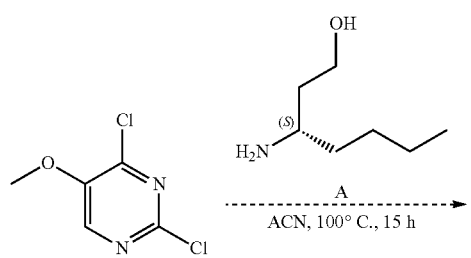

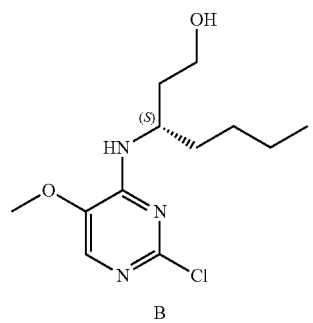

Into a 50 mL vial equipped with a magnetic stir bar was placed 2,4-dichloro-5-methoxypyrimidine (2.0 g, 11.7 mmol), and acetonitrile (20 mL), diisopropylethylamine (3.02 g, 23.4 mmol) and (S)-3-aminoheptanol (4.59 g, 35.1 mmol). The reaction mixture was allowed to stir 15 hours at room temperature. The solvents were removed under reduced pressure. The crude was purified via silica gel column chromatography using a dichloromethane to 10% methanol in dichloromethane gradient. The best fractions were pooled and the solvents were removed under reduced pressure to afford a white solid, B.

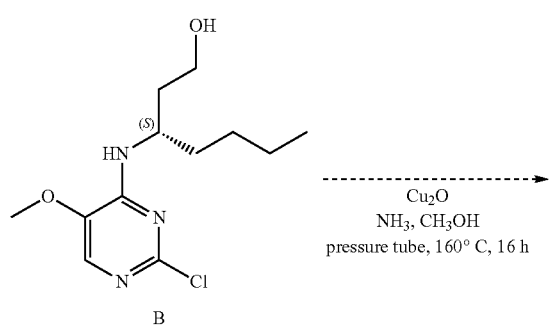

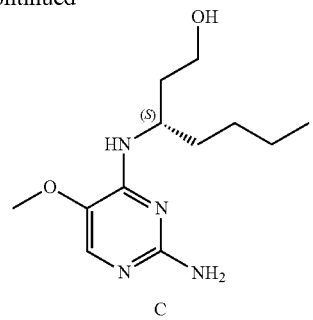

To a thick wall glass vial equipped with a magnetic stir bar was added B (1 g, 3.66 mmol), NH$_3$ (10 mL, aq.), ammonium bicarbonate (3.34 g, 42.3 mmol) and copper(I) oxide (121 mg, 0.85 mmol). The vial was sealed and placed into an oil bath and heated to 150° C. for 15 hours. The reaction mixture was extracted with dichloromethane (3×25 mL), the organic layers were pooled and dried over magnesium sulfate. The solids were removed by filtration and the solvents of the filtrate were removed under reduced pressure. Crude C was purified via HPLC.

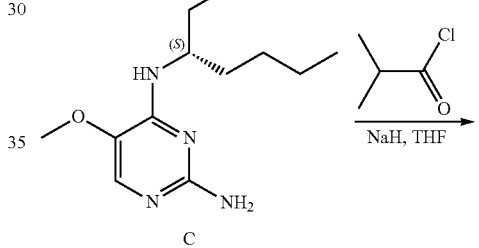

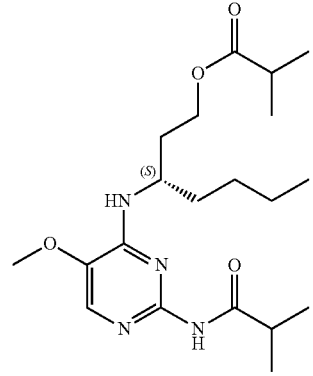

C (463 mg, 1.82 mmol) was dissolved in THF (13 mL) and cooled to −78° C. NaH (145 mg, 3.64 mmol, a 60% dispersion in mineral oil) was added in one portion and stirred at −78° C. for 30 minutes. Isobutyryl chloride (389 µL, 3.64 mmol) was added dropwise at −78° C. and stirred for 10 minutes. The cooling bath was removed and the mixture was allowed to reach room temperature. The mixture was stirred at room temperature for 30 minutes. The mixture was quenched with water and concentrated in vacuo. The residue was purified by HPLC (RP Vydac Denali C18 10 µm, 200 g, 5 cm, mobile phase 0.25% NH$_4$ HCO₃ solution in water, acetonitrile), the desired fractions were collected, and the solvents were removed under reduced pressure to afford the pure product.

LC-MS m/z=395 (M+H), Retention time 1.1 minutes, LC method A.

¹H NMR (400 MHz, DMSO-$d_6$) δ ppm 0.83 (t, J=6.90 Hz, 3H) 0.98-1.07 (m, 12H) 1.16-1.35 (m, 4H) 1.44-1.62 (m, 2H) 1.84 (q, J=6.78 Hz, 2H) 2.45 (spt, J=7.00 Hz, 1H) 2.96 (br. s., 1H) 3.80 (s, 3H) 3.92-4.07 (m, 2H) 4.18-4.31 (m, 1H) 6.69 (d, J=9.03 Hz, 1H) 7.60 (s, 1H) 9.49 (s, 1H).

Synthetic Scheme for the Preparation of A

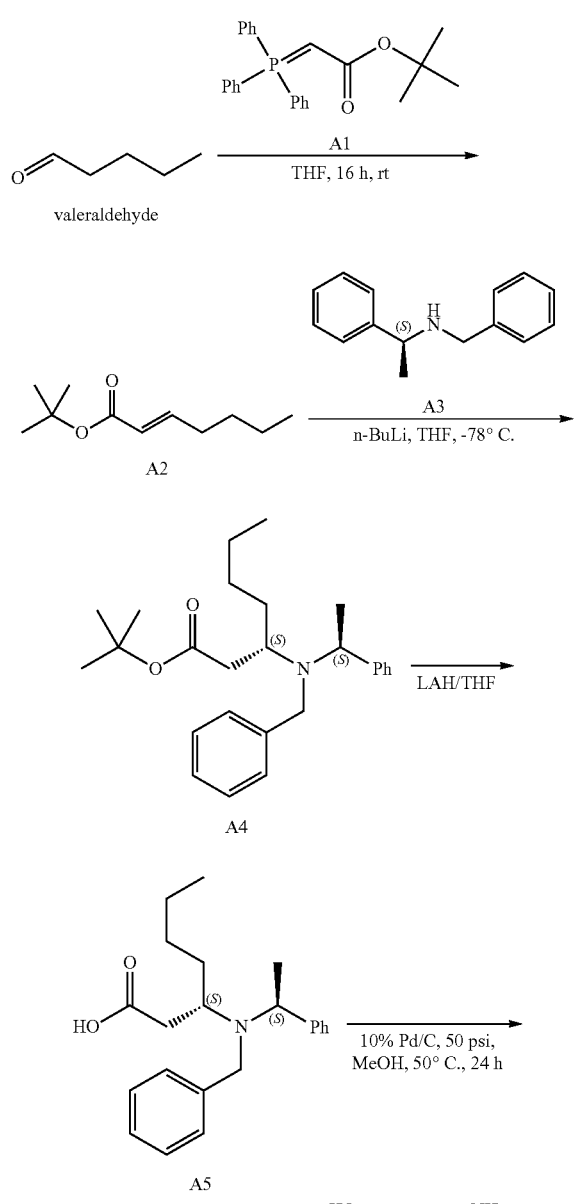

Preparation of A2

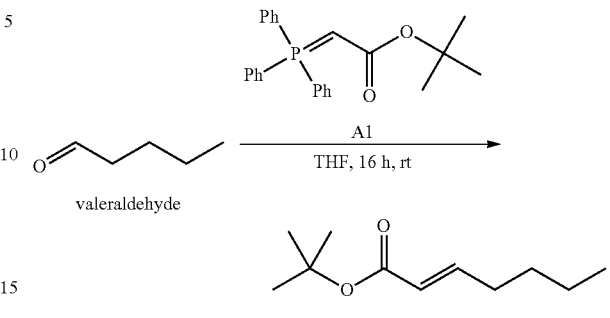

To a solution of valeraldehyde (43 g, 500 mmol) in THF (1 L) was added A1 (200 g, 532 mmol) and the reaction mixture was stirred for 16 hours at room temperature. The solvents were evaporated and the residue was diluted in petroleum ether and filtered. The solvents of the filtrate were removed under reduced pressure and the residue was purified by silica chromatography using a petroleum ether to 3% ethyl acetate in petroleum ether gradient to give A2 (90 g) as a colorless oil.

¹H NMR (400 MHz, CDCl₃): δ ppm 6.81-6.77 (m, 1H), 5.68-5.64 (td, J=1.2 Hz, 15.6 Hz, 1H), 2.11-2.09 (m, 2H), 1.41 (s, 9H), 1.38-1.26 (m, 4H), 0.85-0.81 (t, J=7.2 Hz, 3H).

Preparation of Compound A4

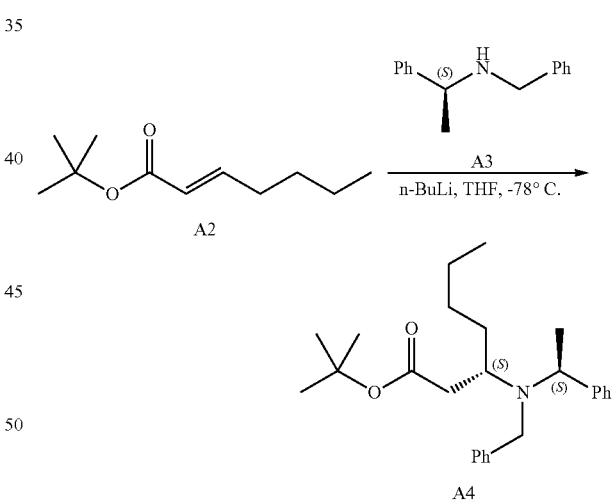

n-butyl lithium (290 mL, 725 mmol) was added to a stirred solution of A3 (165 g, 781 mmol) in THF (800 mL) at −78° C. The reaction mixture was stirred for 30 minutes then A2 (90 g, 488.4 mmol) in THE (400 mL) was added and the reaction was stirred for 2 hours at −78° C. The mixture was quenched with sat., aq. NH₄Cl solution and warmed to room temperature. The product was partitioned between ethyl acetate and water. The organic phase was washed with brine, dried and evaporated. The residue was purified by column chromatography eluting with 5% ethyl acetate in petroleum ether to afford a colorless oil, A4 (132 g).

¹H NMR (400 MHz, CDCl₃): δ ppm 7.36-7.16 (m, 10H), 3.75-3.70 (m, 2H), 3.43-3.39 (d, J=15.2 Hz, 1H), 3.33-3.15

(m, 1H), 1.86-1.80 (m, 2H), 1.47-1.37 (m, 2H), 1.32 (s, 9H), 1.26-1.17 (m, 7H), 0.83-0.79 (t, J=7.2 Hz, 3H).

Preparation of A5

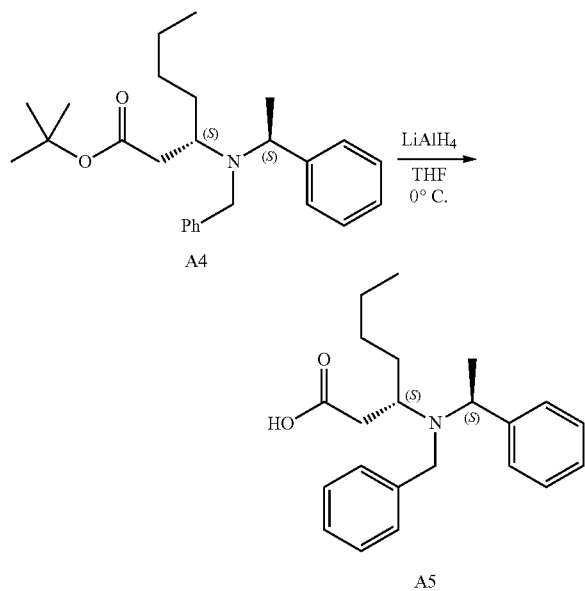

A4 (130 g, 328 mmol) was dissolved in THF (1.5 L) and LAH (20 g, 526 mmol) was added at 0° C. in small portions. The resulting mixture was stirred at the same temperature for 2 hours and then allowed to warm to room temperature. The mixture was quenched with a sat. aq. NH$_4$Cl solution. The product was partitioned between ethyl acetate and water. The organic phase was washed with brine, dried and evaporated. The combined organic layers were dried over sodium sulfate, the solids were removed via filtration and concentrated to afford crude A5 (100 g), which was used in the next step without further purification.

$^1$H NMR (400 MHz, CDCl$_3$): δ ppm 7.33-7.14 (m, 10H), 3.91-3.86 (m, 1H), 3.80-3.77 (d, J=13.6 Hz, 1H), 3.63-3.60 (d, J=13.6 Hz, 1H), 3.43-3.42 (m, 1H), 3.15-3.10 (m, 1H), 2.70-2.63 (m, 2H), 1.65-1.28 (m, 10H), 0.89-0.81 (m, 3H).

Preparation of A

A solution of A5 (38 g, 116.75 mmol) and 10% Pd/C in methanol (200 mL) was hydrogenated under 50 PSI hydrogen at 50° C. for 24 hours. The reaction mixture was filtered and the solvent was evaporated to give A.

$^1$H NMR (400 MHz, DMSO-d$_6$): δ ppm 8.04 (s, 3H), 3.60-3.49 (m, 2H), 3.16-3.15 (m, 1H), 1.71-1.67 (m, 2H), 1.60-1.55 (m, 2H), 1.33-1.26 (m, 4H), 0.90-0.87 (t, J=6.8 Hz, 3H).

Analytical Method.

Compounds 1-8 in the table below were characterized by LC-MS according to the following LC-MS method.

Reverse phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (10 mM ammonium acetate in H$_2$O/acetonitrile 95/5; mobile phase B: acetonitrile) were used to run a gradient condition from 95% A and 5% B to 5% A and 95% B in 1.3 minutes and hold for 0.7 minutes. An injection volume of 0.75 μL was used. Cone voltage was 30 V for positive ionization mode and 30 V for negative ionization mode.

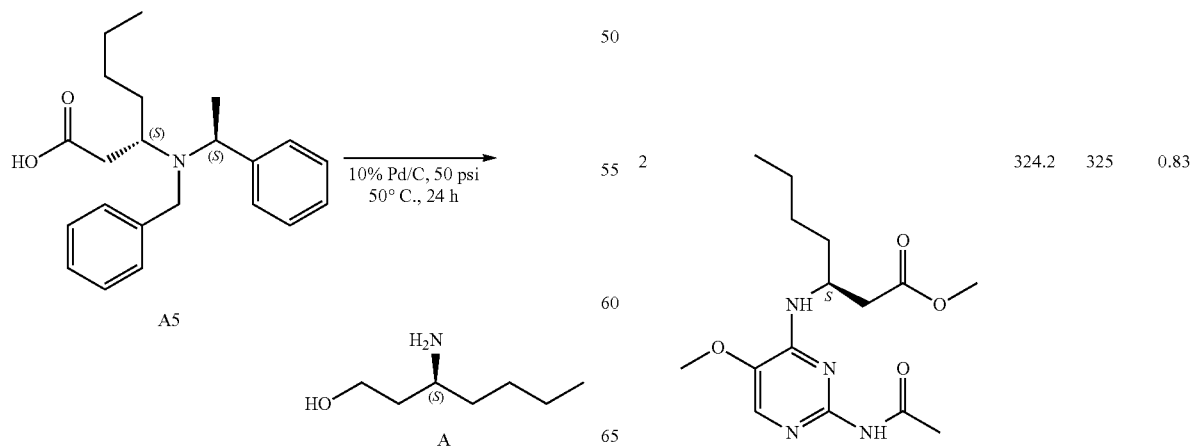

| | STRUCTURE | Exact Mass | LC-MS Mass Found [M + H] | LC-MS Ret Time (min) |
|---|---|---|---|---|
| 1 | 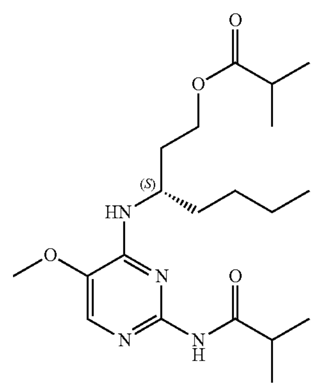 | 394.5 | 395 | 1.1 |
| 2 | 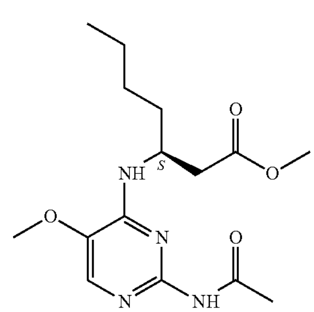 | 324.2 | 325 | 0.83 |

| | STRUCTURE | Exact Mass | Mass Found [M + H] | LC-MS Ret Time (min) |
|---|---|---|---|---|
| 3 | (structure) | 358.2 | 359 | 0.88 |
| 4 | (structure) | 372.2 | 373 | 0.94 |
| 5 | (structure) | 314.2 | 315 | 1.2 |
| 6 | (structure) | 373.2 | 374 | 0.7 |
| 7 | (structure) | 419.2 | 420 | 0.73 |
| 8 | (structure) | 358.2 | 359 | 0.89 |

Production of IFN-α and Up-Regulation of CXCL10 mRNA In Vivo

The potential of compounds to induce IFN-α production and CXCL10 mRNA up-regulation in vivo was evaluated after oral administration to C57BL/6 mice. The quantity of IFN-α in systemic circulation was followed over time, using a murine pan-IFN-α ELISA (PBL InterferonSource, ref. 42120). This ELISA recognizes all murine IFN-α subtypes. CXCL10 is an interferon-stimulated gene (ISG) whose expression is highly induced upon binding of IFN-I to the receptor IFNAR (interferon alpha receptor). CXCL10 mRNA expression levels were followed by RT-qPCR.

For each compound and dose tested, 3 female C57BL/6J mice, from 6-10 weeks of age, 20-22 g of body weight were tested. Animals were given compound 1 as a single oral dose of 15.5 mg/kg as a 1.55 mg/mL solution in 20% aqueous hydroxypropyl β-cyclodextrin vehicle using a feeding tube. 0.5, 1, 2, 4 and 7 hours after dosing, systemic blood was drawn from the tail vein into K-EDTA containing tubes. Plasma was separated from blood cells by centrifugation at 1500 g, 10 min, 4° C. and stored at −80° C. prior to ELISA analysis. At each time point, the median and standard deviation over the 3 animals was calculated to evaluate the potency of the compound.

Blood was also drawn from the tail vein into micronic tubes containing 500 μl of PAXgene solution (PAXgene blood RNA tubes from PreAnalytix). After overnight incubation at room temperature, the tubes were stored at −20° C. before total RNA extraction with the PAXgene 96 Blood RNA kit (PreAnalytix). Purified RNA was reverse transcribed using random 6-mer primers (High-Capacity cDNA Archive kit, Applied Biosystems). CXCL10 mRNA levels were by Taqman qPCR technology (Taqman universal PCR master mix, no UNG AmpErase and Taqman Gene Expression assay Mm00445235_m1 from Applied Biosystems) on a 7900HT Fast Real-time PCR system (Applied Biosystems). HPRT1 (hypoxanthine phosphoribosyltransferase 1) mRNA levels were used as endogenous control (Mm01545399_m1). The ΔΔCt method (for relative quantification) was used to evaluate regulation of CXCL10 expression by the compound compared to the vehicle control. At each time point, the median and standard deviation over the 3 animals was calculated to evaluate the potency of the compounds.

The invention claimed is:
1. A compound selected from the group consisting of:
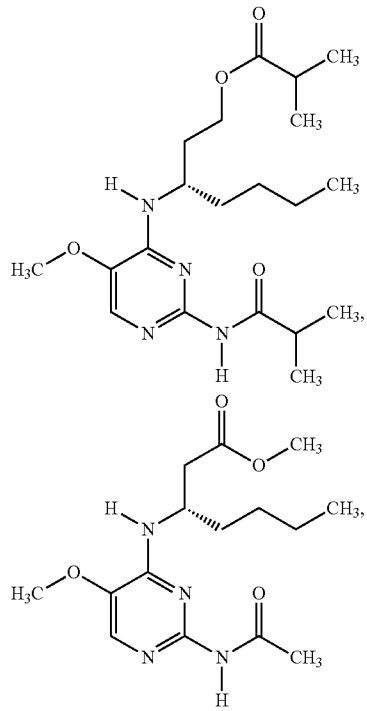
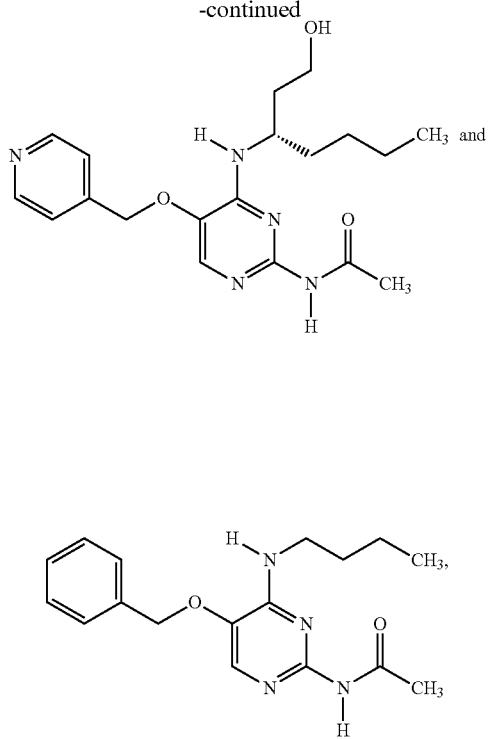
or a pharmaceutically acceptable salt thereof.
* * * * *